US00PP32984P3

(12) United States Plant Patent
Knapp et al.

(10) Patent No.: US PP32,984 P3
(45) Date of Patent: Apr. 20, 2021

(54) STRAWBERRY PLANT NAMED 'UCD VALIANT'

(50) Latin Name: ***Fragaria* x *ananassa* Duchesne**
Varietal Denomination: UCD Valiant

(71) Applicant: The Regents of the University of California, Oakland, CA (US)

(72) Inventors: Steven J. Knapp, Davis, CA (US); Glenn S. Cole, Davis, CA (US); Douglas V. Shaw, Davis, CA (US); Kirk D. Larson, Santa Ana, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/501,375

(22) Filed: Apr. 1, 2019

(65) Prior Publication Data

US 2019/0380246 P1 Dec. 12, 2019
US 2020/0178445 P9 Jun. 4, 2020

Related U.S. Application Data

(60) Division of application No. 15/932,994, filed on Jun. 7, 2018, which is a continuation of application No. 15/530,135, filed on Dec. 6, 2016, now abandoned, which is a continuation of application No. 14/545,653, filed on Jun. 3, 2015, now abandoned.

(60) Provisional application No. 61/999,632, filed on Jul. 30, 2014, provisional application No. 61/997,548, filed on Jun. 4, 2014.

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 6/7409
See application file for complete search history.

*Primary Examiner* — Anne Marie Grunberg
(74) *Attorney, Agent, or Firm* — Kilpatrick Townsend & Stockton LLP

(57) ABSTRACT

'UCD Valiant' is a day-neutral cultivar of a strawberry plant that provides high yields and produces large, firm fruit. The variety has performed particularly well in low-input and organic production systems.

7 Drawing Sheets

Genus and species: The strawberry cultivar of this invention is botanically identified as *Fragaria* X *ananassa* Duchesne.

Variety denomination: The variety denomination is 'UCD Valiant'.

BACKGROUND OF THE INVENTION

This invention relates to a new and distinct day-neutral strawberry cultivar designated as 'UCD Valiant', which originated from a cross performed in the winter of 2011 between 'Merced' (U.S. Plant Pat. No. 25,436) and proprietary germplasm parent 07C092P003 (unpatented). Seeds of the cross were harvested from greenhouse-grown plants in the spring of 2011 and germinated in June 2011. Seedlings were transplanted to a greenhouse in July 2011 and transplanted to the field in October 2011. 'UCD Valiant' was selected and clones were first harvested in 2012. 'UCD Valiant' has been asexually propagated since 2012.

The plant of this selection was originally designated '11C103P001' (also represented as 11.103-1) and later called '16DN011' or 'UC11' for evaluation in field trials. 'UCD Valiant' was also called '15 MBA-3' for certain testing trials.

BRIEF SUMMARY OF THE INVENTION

'UCD Valiant' is a day-neutral (ever-bearing) strawberry cultivar selected for increased marketable fruit yield, earliness, and extended shelf-life. 'UCD Valiant' provides higher yields in low-input and organic production systems, and produces fruit earlier than other high yielding day-neutral cultivars in the southerly locations in the coastal California day-neutral environments. 'UCD Valiant' exhibits earlier flowering and increased numbers of stolons compared to parent 07C092P003, and is day neutral compared to short day parent Merced.

'UCD Valiant' produces fruit earlier than 'Cabrillo' (U.S. Plant Pat. No. 27,830) and produces more marketable fruit per hectare compared to 'Monterey' (U.S. Plant Pat. No. 19,767) and 'Cabrillo'. 'UCD Valiant' exhibits an early season yield spike in the southernmost day-neutral environments tested compared to the yields for 'UCD Moxie' (U.S. Plant patent application Ser. No. 16/501,376), although the cumulative marketable yields of 'UCD Valiant' are not significantly different from those of 'UCD Royal Royce' (U.S. Plant patent application Ser. No. 16/501,374) or 'UCD Moxie'. 'UCD Valiant' is a day-neutral cultivar, whereas parent variety 'Merced' is a short-day cultivar.

'UCD Valiant' was genotyped with a 35,000-SNP array (Hardigan et. al., *Plant Genome* 11:180049, 2018). The variety has a unique DNA profile compared to 'Cabrillo', 'Monterey', 'UCD Royal Royce', and 'UCD Moxie'. The pairwise genetic distances between 'UCD Valiant' and 'UCD Moxie', 'UCD Royal Royce', 'Cabrillo', and 'Monterey' are estimated to be 0.223, 0.270, 0.307, and 0.266, respectively based on the 35,000-SNP genotype analysis.

'UCD Valiant' also has a unique DNA profile compared to each of its parents, 'Merced' and proprietary germplasm variety 07C092P003.

'UCD Valiant' is maintained by annual asexual propagation by stolons in Winters, Calif.

BRIEF DESCRIPTION OF THE DRAWINGS

The colors in the photograph are depicted as nearly true as is reasonably possible to obtain in color reproductions of this type.

DETAILED DESCRIPTION OF THE INVENTION

Fruit Production

Figure 1:
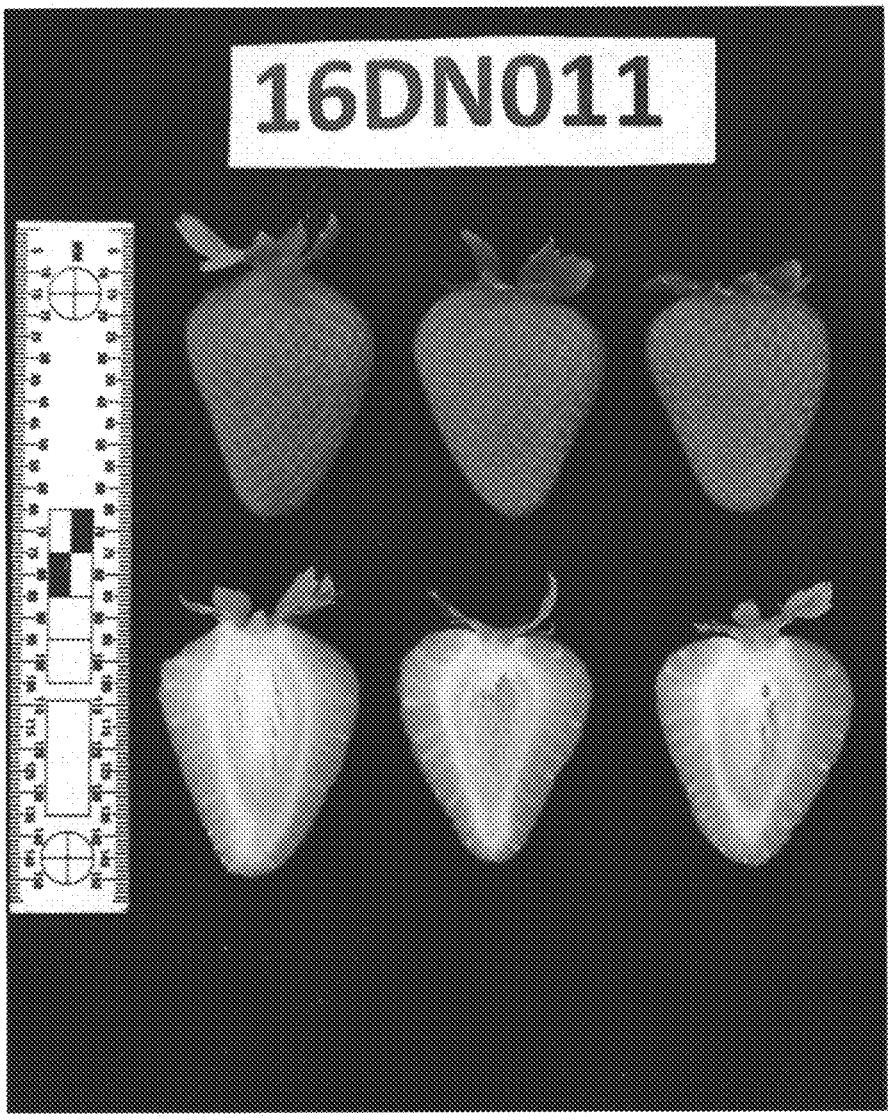
FIG. 1 shows fruit of 'UCD Valiant' in cross-section.
Figure 2:
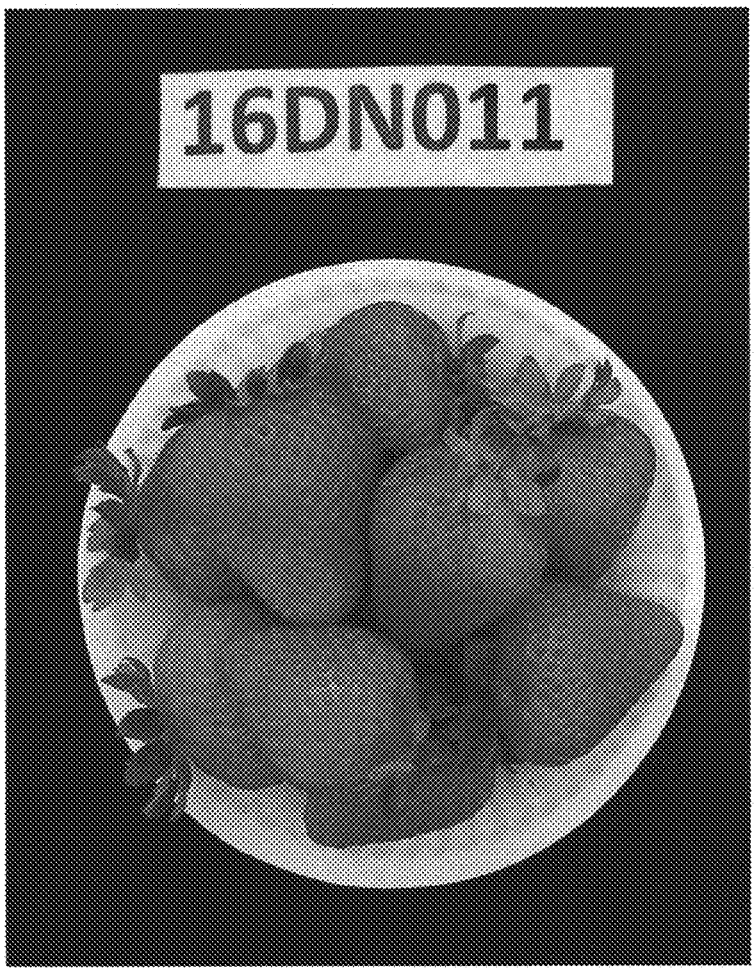
FIG. 2 illustrates color of the fruit.
Figure 3:
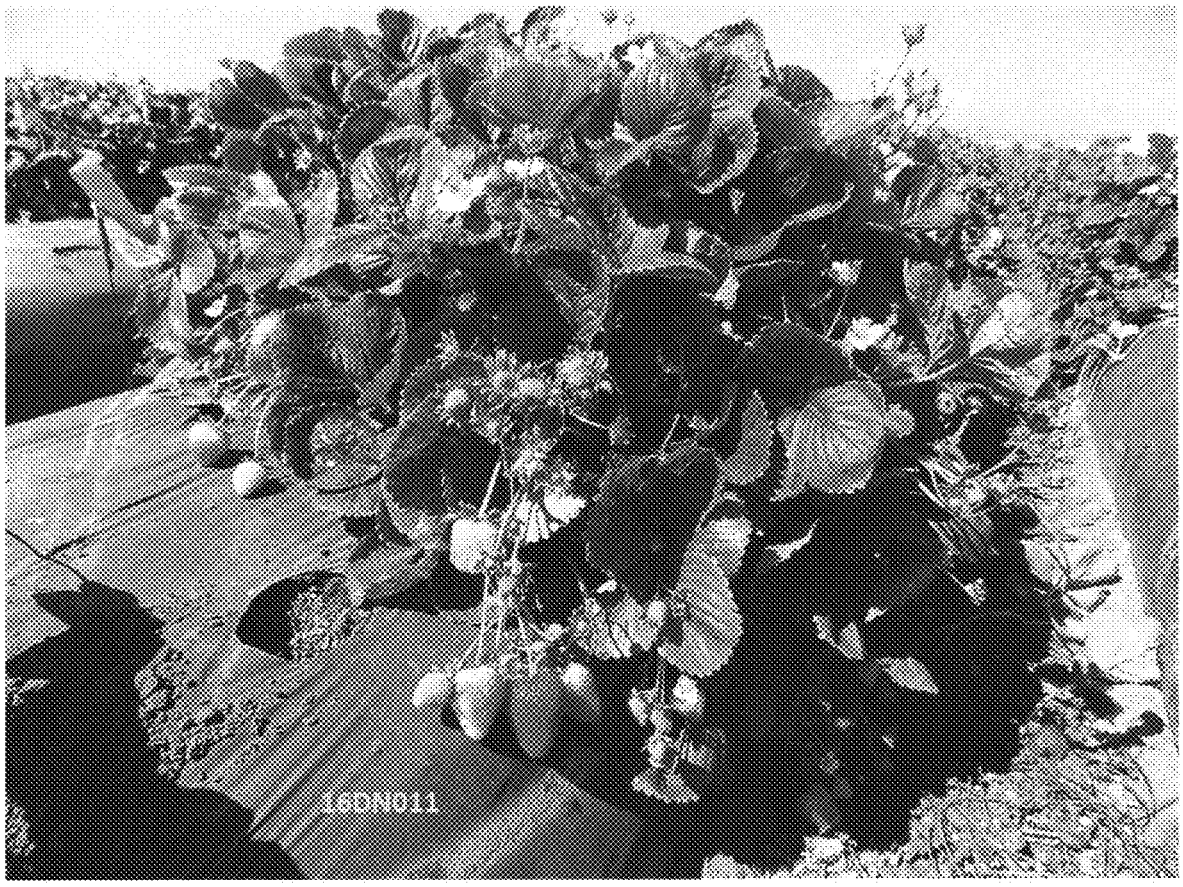
FIG. 3 depicts general flowering and fruiting characteristics of 'UCD Valiant'.
Figure 4:
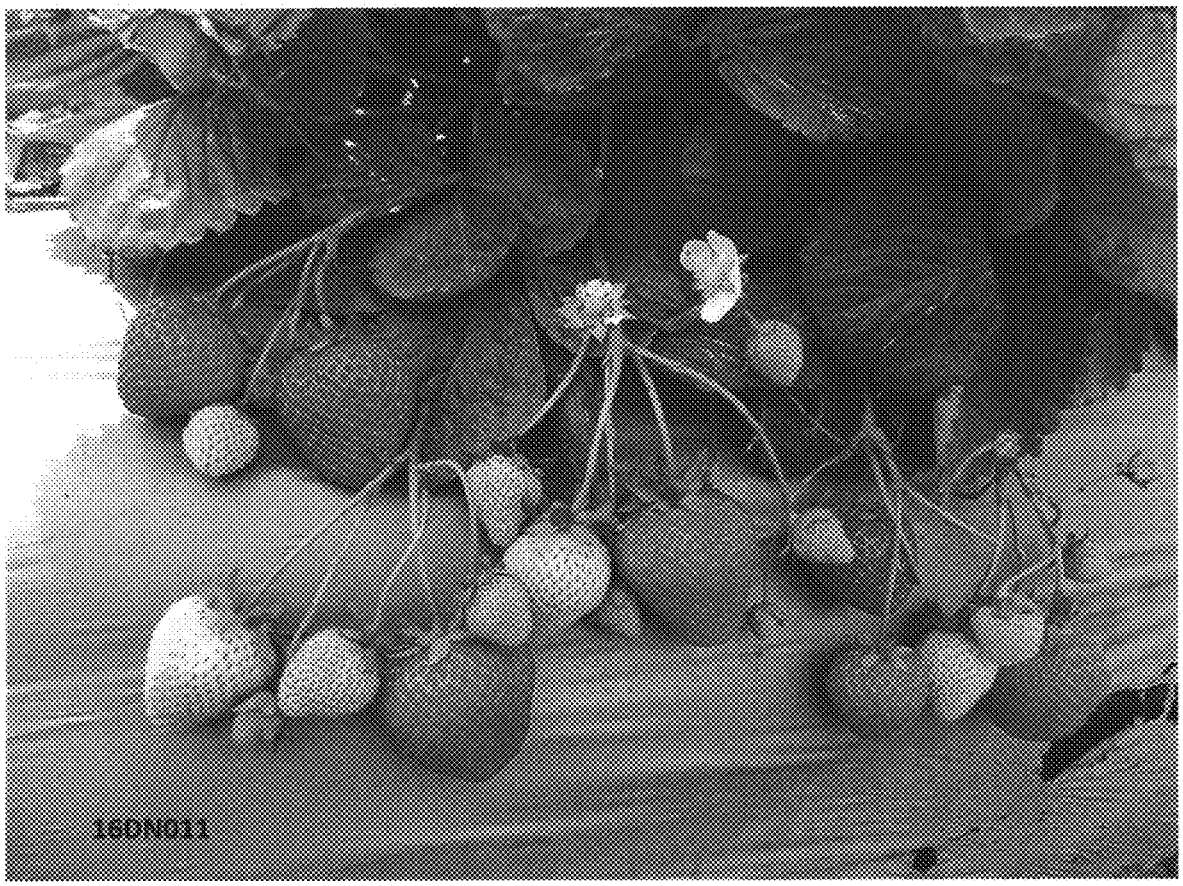
FIG. 4 shows representative fruit trusses of the plant.
Figure 5:
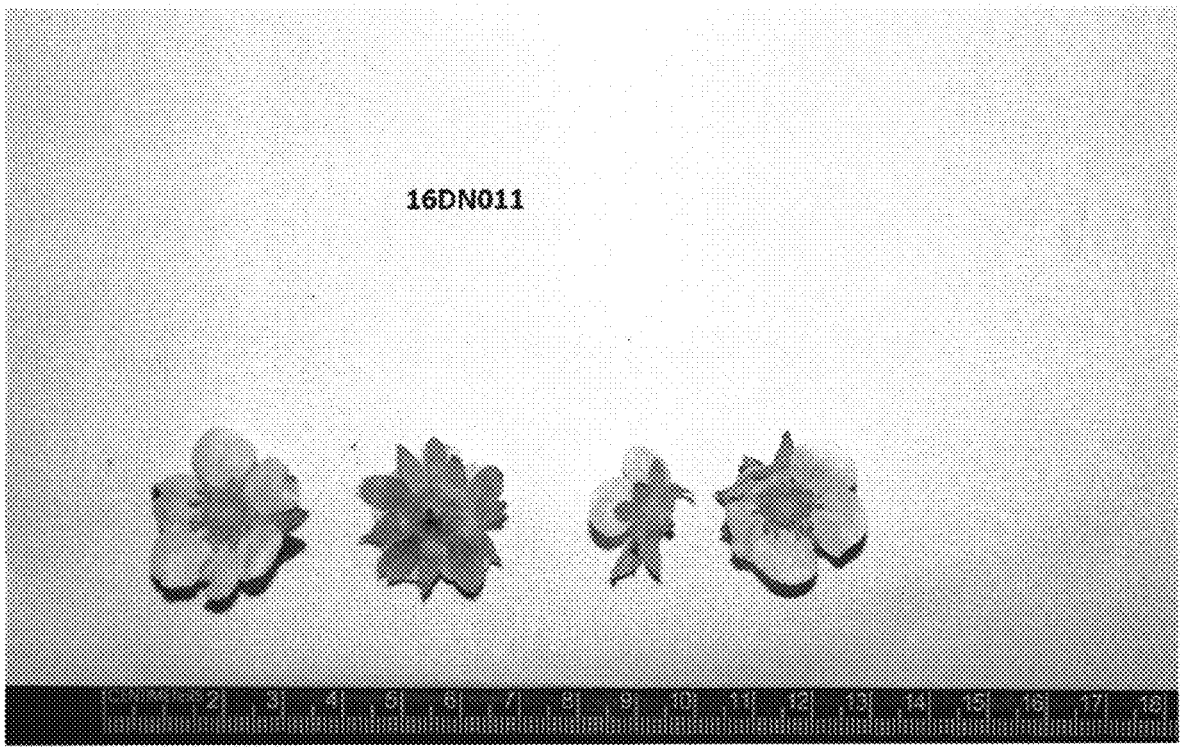
FIG. 5 shows representative flowers of the plant.
Figure 6:
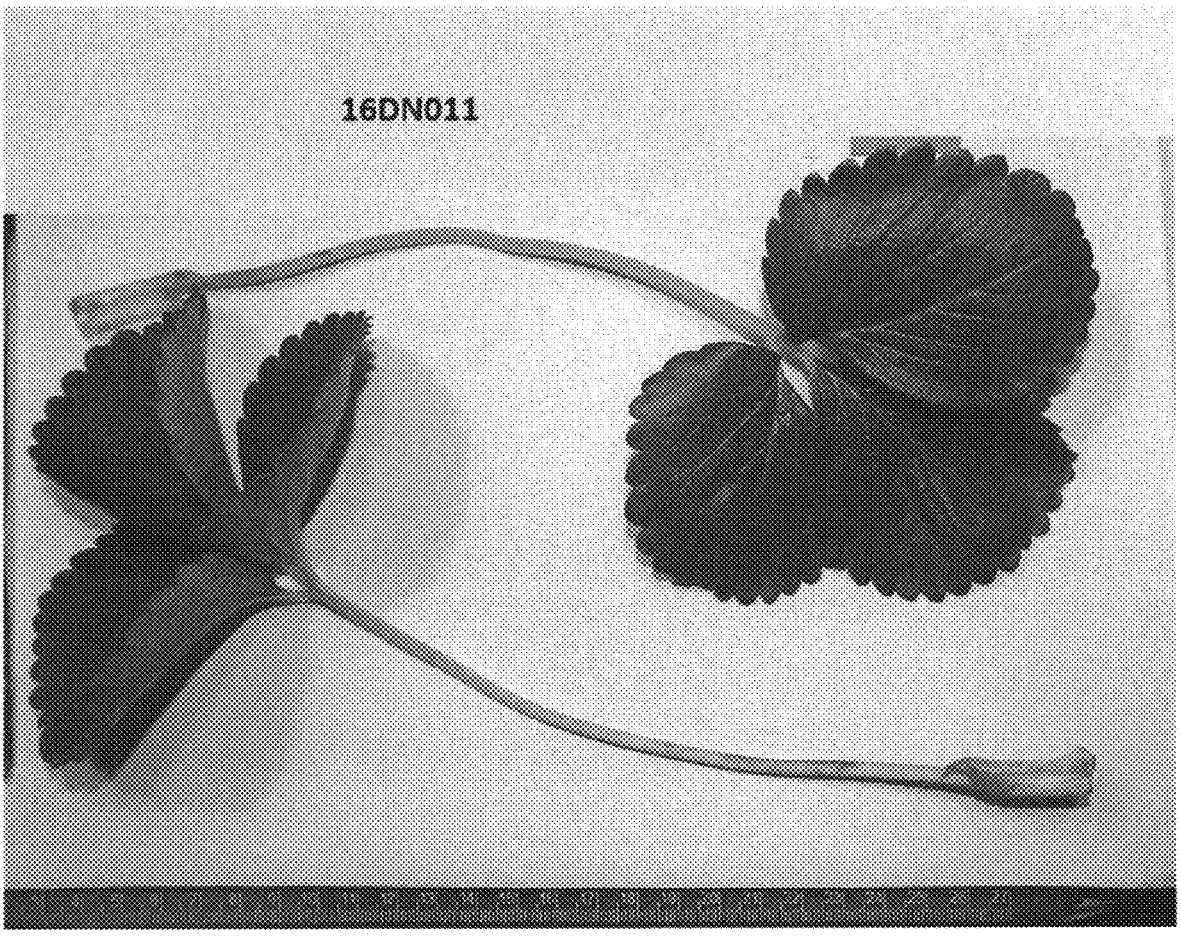
FIG. 6 shows representative leaves of the plant.
Figure 7:
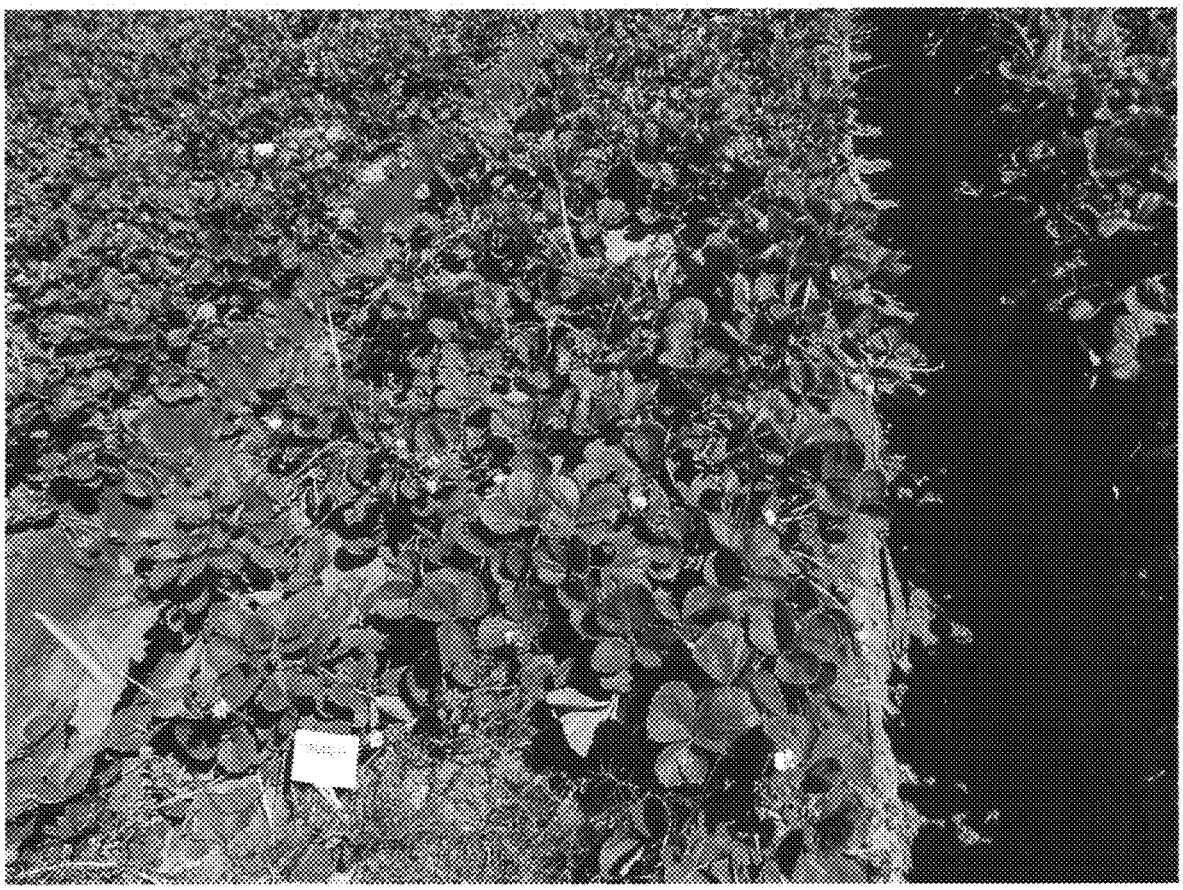
FIG. 7 depicts plant habit.

'UCD Valiant' and comparison cultivars were asexually propagated in high-elevation nurseries in Dorris and Mcdoel, Calif. for field testing in 2015-2016, 2016-2017, and 2017-2018. Clones were harvested according to commercial planting schedules, which were calibrated by the number of chill hours required for optimum production in Santa Maria and Prunedale, Calif.

Cultivar testing in small-plot yield trials was performed as follows. Test day-neutral cultivars and comparison cultivars were field tested in Oso Flaco (Santa Maria, Calif.) and Prunedale, Calif. in 2015-2016. Fruit was harvested once or twice per week over the spring and summer growing season: March 16 to Aug. 18, 2016 in Santa Maria (31 harvests) and April 2 to Aug. 27, 2016 in Prunedale (30 harvests). 'UCD Valiant' was selected on the basis of fruit appearance, size, shelf-life, and cumulative marketable fruit yield for a second year (2016-17) of replicated testing in Santa Maria and Prunedale (Tables 1-2). Fruit was harvested once or twice per week over the growing season: March 13 to Aug. 21, 2017 in Santa Maria (25 harvests) and April 3 to Sep. 1, 2017 in Prunedale (44 harvests in Prunedale). To highlight differences among cultivars, the yield data were displayed in three ways: (a) per plant yields for individual harvests for each location x year combination for 'UCD Valiant', 'Monterey', 'San Andreas', and 'Cabrillo'; (b) per plant cumulative marketable yields for 'UCD Valiant', 'Monterey', 'San Andreas', and 'Cabrillo'; and (c) per plant cumulative marketable yields tested in both years and locations. Entry ranks were highly consistent and the best and worst performing cultivars were virtually identical over locations and years.

Table 1 shows marketable yield (g/plant) for 'UCD Valiant' compared to that for 'Monterey', 'San Andreas' (U.S. Plant Pat. No. 19,975), and 'Cabrillo' tested in small-plot yield trials in Santa Maria, Calif. and Prunedale, Calif. in 2015-16 and 2016-17.

Table 2 shows the range in increase in yield compared to 'Monterey', 'San Andreas', and 'Cabrillo' for the small-plot yield trials.

TABLE 1

Least-square means for cumulative marketable yield tested in small-plot yield trials in Santa Maria, CA and Prunedale, CA in 2015-2016 and 2016-2017

| | Santa Maria | | Prunedale | | Yield across Locations and Years |
|---|---|---|---|---|---|
| Cultivar | 2015-16 | 2016-17 | 2015-16 | 2016_17 | (g/plant) |
| UCD Valiant | 1,984 | 2,380 | 1,460 | 2,482 | 2,078 |
| Cabrillo | 1,617 | 2,073 | 1,362 | 2,299 | 1,838 |
| Monterey | 1,115 | 1,324 | 1,077 | 1,722 | 1,310 |
| San Andreas | 1,229 | 1,096 | 1,048 | 1,569 | 1,236 |

TABLE 2

Least-square means for cumulative marketable yield (g/plant) across years and locations in the small-plot yield trials. The ranges for yield increases over comparison cultivars were estimated from least square means for individual environments (see, Table 1). (Percent Marketable Fruit = (Cumulative Marketable Fruit Yield)/(Cumulative Total Fruit Yield)

| Cultivar | Yield (g/plant) | Percent Marketable Fruit | Yield Increase Range Over San Andreas | Yield Increase Range Over Monterey | Yield Increase Range Over Cabrillo |
|---|---|---|---|---|---|
| UCD Valiant | 2,078 | 84-86 | 39-117% | 35-80% | 7-22% |
| Cabrillo | 1,838 | 86-87 | | | |
| Monterey | 1,310 | 79-82 | | | |
| San Andreas | 1,236 | 76-84 | | | |

The cumulative marketable fruit yields of 'UCD Valiant' were significantly greater than 'Monterey' ($p<0.0001$), 'San Andreas' ($p<0.0001$) and 'Cabrillo' ($p<0.055$) across years and locations (Table 1). The per plant yields of 'UCD Valiant' were 7 to 117% greater than 'Cabrillo', 'Monterey', and 'San Andreas' (Table 2). The mean fruit size for 'UCD Valiant' (35.3 g/fruit) was significantly different from 'Cabrillo' (30.0 g/fruit; $p<0.0001$), Monterey (28.4 g/fruit $p<0.0001$), and 'San Andreas' (26.7 g/fruit; $p<0.0001$).

The marketable fruit percentages for 'UCD Valiant' and 'Cabrillo' were comparable (84-87%) and superior to 'Monterey' and 'San Andreas' (76 to 84%) (Table 2).

'UCD Valiant' was selected, with other test varieties, for advanced testing in large-plot yield trials (150 plants/plot) with five commercial growers in 2017-18. The selection criteria were: high cumulative marketable yields, high marketable fruit percentages, resistance to bruising and deterioration with harvest, handling, and storage, fruit appearance, and reduced runner production in coastal production environments. The production systems for large-plot yield trials were diverse and included: low-input organic (Santa Maria, Calif.), low-input fumigated (Salinas, Calif.), and high-input fumigated (Oso Flaco, Calif., Prunedale, Calif. and Moss Landing, Calif.). Fruit was harvested from February 2 to October 5 in Oso Flaco (52 harvests), April 3 to October 4 in Santa Maria (53 harvests), April 12 to October 6 in Prunedale (48 harvests), May 7 to October 8 in Moss Landing (45 harvests), and March 9 to October 12 in Salinas (36 harvests). The residual for statistical analyses was the entry x location interaction mean square.

TABLE 3

Least square means for cumulative marketable fruit yield (cartons/acre) for 'UCD Valiant', 'Monterey', and 'Cabrillo' grown in unreplicated large-plot (150 plant) yield trials in five locations in 2017-18, where a carton = eight clamshells and eight clamshells/carton x one pound/clamshell = eight pounds/carton.

| Cultivar | Salinas | Santa Maria | Oso Flaco | Prunedale | Mossing Landing | Across Locations |
|---|---|---|---|---|---|---|
| UCD Valiant | 11,241 | 11,490 | 16,155 | 16,135 | 8,878 | 12,780 |
| Cabrillo | 5,201 | 6,892 | 17,569 | 14,057 | 9,465 | 10,637 |
| Monterey | NA | 7,891 | 14,731 | 11,940 | 10,257 | 10,274 |

TABLE 4

Least square means for fruit weight (g/fruit) for 'UCD Valiant', 'Monterey', and 'Cabrillo' grown in unreplicated large-plot (150 plant) yield trials in in five locations in 2017-18, where fruit weight = (weight of fruit per clamshell)/(number of fruit per clamshell).

| Cultivar | Salinas | Santa Maria | Oso Flaco | Prune-dale | Mossing Landing | Across Locations |
|---|---|---|---|---|---|---|
| UCD Valiant | 31.2 | 24.3 | 32.1 | 31.2 | 38.7 | 31.5 |
| Cabrillo | 26.1 | 21.9 | 28.0 | 27.5 | 34.0 | 27.5 |
| Monterey | NA | 21.6 | 29.4 | 27.9 | 33.8 | 27.8 |

TABLE 5

Statistical significance (Pr > F) of differences between least square means for cumulative fruit yield (cartons/acres) and fruit weight (g/fruit) for 'UCD Valiant', 'Monterey', and 'Cabrillo'tested in unreplicated large-plot (150 plant) yield trials in five locations in 2017-18.

| | Yield | | Fruit Weight (g/fruit) | |
|---|---|---|---|---|
| Comparison | Difference (carton/acre) | Pr > F | Difference (g/fruit) | Pr > F |
| UCD Valiant-Monterey | 2,506 | 0.0203 | 3.68 | <0.0001 |
| UCD Valiant-Cabrillo | 2.143 | 0.0307 | 4.01 | <0.0001 |

The mean cumulative marketable yield of 'UCD Valiant' was 12,780 cartons/acre=102,240 pounds/acre across production systems and locations (Table 3). The cumulative marketable fruit yields of 'UCD Valiant' were significantly greater than 'Monterey' (p=0.02) and 'Cabrillo' (p=0.03) across production systems and environments. 'UCD Valiant' produced 2,506 cartons/acre more than 'Monterey' (p=0.008) and 2,143 cartons/acre more than 'Cabrillo' (Tables 3 & 5). 'UCD Valiant' provided high yields in both of the low-input production systems tested (Santa Maria and Salinas). 'UCD Valiant' fruit weights were significantly larger than 'Monterey' (p<0.0001) and 'Cabrillo' (p<0.0001) (Tables 4 & 5).

To assess the quality of freshly harvested fruit, firmness (grams force), total soluble solids (SS) concentration, and titratable acid (TA) concentrations were measured from samples of fruit harvested on three dates from each location in 2017-18 (Tables 6-7). Harvest dates were one month apart with one replication per harvest date, 10 sub-samples per replication for firmness, and three subsamples per replication for SS and TA. Firmness was quantified with a hand-held penetrometer measuring the grams of force needed to puncture the fruit. SS and TA concentrations were quantified with benchtop instruments. The SS to TA ratio provides a relative measure of sweetness. To assess shelf-life, fruit weight (g/clamshell), SS, brightness (ordinal scale with 1=excellent to 5=unmarketable), liquid leakage (g/clamshell), and mold incidence (%) were quantified from samples of fruit harvested on two dates from each location with fruit stored under standard 4° C. conditions for 0, 7, 14, and 21 days (Table 8). Harvest dates were one month apart with one replication per harvest date.

TABLE 6

Least-square means (LSMs) for firmness, soluble solids concentration (SS), and titratable acid concentration (TA) for 'UCD Valiant', 'Monterey', and 'Cabrillo' grown in five locations in 2017-18. LSMs were estimated from three harvest dates per location, one biological replication per harvest date, 10 sub-samples per harvest date for firmness, and three sub-samples per harvest date for SS and TA.

| Cultivar | Firmness (g force) | SS (%) | Titrable Acids (g/100 ml) | SS/TA |
|---|---|---|---|---|
| UCD Valiant | 377.44 | 7.62 | 0.83 | 9.19 |
| Cabrillo | 359.61 | 8.05 | 0.77 | 10.50 |
| Monterey | 294.55 | 8.71 | 0.77 | 11.48 |

TABLE 7

Statistical significance (Pr > F) of differences between least square means for SS, TA, and SS/TA for 'UCD Valiant', 'Monterey', and 'Cabrillo' tested in unreplicated large-plot yield trials in five locations in 2017-18.

| | Soluble Solids Concentration (SS) | | Titratable Acids Concentration (TA) | | SS/TA | |
|---|---|---|---|---|---|---|
| Com-parison | Least Square Mean Difference (%) | Pr > F | Least Square Mean Difference (g/100 ml) | Pr > F | Least Square Mean Difference | Pr > F |
| UCD Valiant-Monterey | −1.09 | 0.0041 | 0.07 | 0.0147 | −2.29 | <0.0001 |
| UCD Valiant-Cabrillo | −0.43 | 0.2624 | 0.06 | 0.0354 | −1.31 | 0.0028 |

TABLE 8

Least-square means (LSMs) for fruit weight (g/clamshell), soluble solids concentration (SS), fruit brightness, liquid leakage, and mold formation for 'UCD Valiant', 'Monterey', and 'Cabrillo' grown in four locations in 2017-18 and stored for zero to 21 days postharvest. LSMs were estimated from two harvest dates per location

| Cultivar | Days Post-Harvest Storage | Weight (g/clamshell) | Soluble Solids (%) | Bright-ness | Liquid Leakage (g) | Mold (%) |
|---|---|---|---|---|---|---|
| UCD Valiant | 0 | 576.4 | 7.1 | 1.4 | 0.0 | 0.0 |
| Cabrillo | 0 | 555.4 | 7.5 | 1.3 | 0.0 | 0.0 |
| Monterey | 0 | 572.0 | 9.2 | 1.2 | 0.0 | 0.0 |
| UCD Valiant | 7 | 561.1 | 6.7 | 2.6 | 0.0 | 0.0 |
| Cabrillo | 7 | 538.7 | 7.4 | 2.0 | 0.2 | 0.0 |
| Monterey | 7 | 556.3 | 9.1 | 1.8 | 0.0 | 0.0 |
| UCD Valiant | 14 | 546.4 | 7.0 | 3.8 | 0.8 | 1.3 |
| Cabrillo | 14 | 522.9 | 7.3 | 3.3 | 0.8 | 1.2 |
| Monterey | 14 | 542.3 | 9.5 | 3.0 | 0.0 | 0.5 |
| UCD Valiant | 21 | 527.5 | 6.8 | 4.8 | 24.2 | 31.7 |

TABLE 8-continued

Least-square means (LSMs) for fruit weight (g/clamshell), soluble solids concentration (SS), fruit brightness, liquid leakage, and mold formation for 'UCD Valiant', 'Monterey', and 'Cabrillo' grown in four locations in 2017-18 and stored for zero to 21 days postharvest. LSMs were estimated from two harvest dates per location

| Cultivar | Days Post-Harvest Storage | Weight (g/clamshell) | Soluble Solids (%) | Bright-ness | Liquid Leakage (g) | Mold (%) |
|---|---|---|---|---|---|---|
| Cabrillo | 21 | 504.4 | 7.3 | 4.3 | 35.8 | 36.7 |
| Monterey | 21 | 526.4 | 8.7 | 3.8 | 0.2 | 11.8 |

'UCD Valiant' produced fruit meeting or exceeding industry standards for mass-production cultivars (Tables 6-8). The fruit was firm, withstood the rigors of harvest, packing, and storage, and maintained acceptable fruit quality and appearance for over two weeks of storage. 'UCD Valiant' produced significantly firmer fruit than 'Monterey' ($p<0.0001$), but not significantly different from 'Cabrillo' ($p=0.11$). 'UCD Valiant' additionally had significantly lower SS concentration than 'Monterey' ($p<0.004$), but was not significantly different from that of 'Cabrillo' ($p=0.26$). The SS/TA ration for 'UCD Valiant' was significantly lower than 'Monterey' ($p<0.0001$) and 'Cabrillo' ($p=0.0028$).

'UCD Valiant' maintained adequate marketability and visual appeal over 14 days of post-harvest storage, the industry standard (Table 8), as did 'Cabrillo' and 'Monterey'. The marketability of fruit stored for 21 days post-harvest was inadequate for all three cultivars. Fruit weight and brightness significantly decreased as post-harvest storage time increased (Table 8). The fruit weight decreases were not significantly different among cultivars. Cultivar x post-harvest storage time interactions were only statistically significant for liquid leakage and mold formation, with 'Cabrillo' deteriorating more than 'UCD Valiant' and 'Monterey' (Table 8).

Disease Resistance Evaluation

'UCD Valiant' and additional cultivars were screened for resistance to *Fusarium* wilt, *Verticillium* wilt, *Macrophomina*, and *Phytophthora* crown rot in Davis, Calif. field experiments between 2015 and 2018. These included 2015-16 and 2016-17 *Fusarium* wilt screening experiments with 480 to 960 entries, a 2015-16 *Macrophomina* experiment with 960 entries, 2016-17 and 2017-18 *Verticillium* wilt experiments with 480 to 960 entries, and a 2017-18 *Phytophthora* crown rot experiment with 480 entries. Entries were arranged in randomized complete blocks experiment designs with four single-plant replications per entry. The 2015-16 experiments were planted in virgin soil in Davis, Calif. The 2016-17 and 2017-18 experiments were planted in fumigated soils in Davis, Calif. For each experiment, plants were artificially inoculated with the respective pathogen and phenotyped for disease symptoms on an ordinal scale, where 1=highly resistant (symptomless), 2=resistant, 3=intermediate, 4=susceptible, and 5=highly susceptible (dead). Within each experiment, plants were phenotyped at six different time points to study changes in the phenotypic distributions and quantify the progression of disease symptoms over time.

'UCD Valiant' was susceptible to *Fusarium* wilt (4.5 on scale), moderately susceptible to *Verticillium* wilt (3.3 on scale), moderately susceptible to *Phytophthora* crown rot (3.0 on scale), and susceptible to *Macrophomina* (5.0 on scale).

BOTANICAL DESCRIPTION

The following botanical descriptors are characteristic of 'UCD Valiant'. The descriptors were collected from two different sites in May 2017 in Santa Maria, Calif. Colors are designated with reference to The Royal Horticultural Society (R.H.S.) Colour Chart, Sixth Edition, 2015. The characteristics of 'UCD Valiant' may vary in detail, depending upon environmental factors and culture conditions.

Growth habitat: Semi-upright Plant height average of 35 cm. Plant spread average of 40 cm.
Density of foliage: Medium.
Vigor: Strong.
Position of inflorescence in relation to foliage: Above.
Number of stolons: Average of 8.
Stolon, anthocyanin coloration: 60B.
Stolon, density of pubescence: Sparse.
Leaf size: Medium.
Leaf color: Adaxial 143A, Abaxial 138B.
Leaf blistering: Medium.
Leaf glossiness: Medium glossy.
Leaf variegation: Absent.
Terminal leaflet, length in relation to width: Average of 80 mm long and 76 mm wide.
Terminal leaflet, shape of base: Obtuse.
Terminal leaflet, margin: Serrate to crenate.
Terminal leaflet, shape in cross section: Concave.
Petiole, length: Average of 20 cm.
Petiole, attitude of hairs: Upwards.
Stipule, anthocyanin coloration: Core color 144D, Margin color 144A (absent or weak).
Inflorescence, number of flowers: Many.
Pedicel, attitude of hairs: Upwards.
Pedicel, anthocyanin coloration: 60B.
Flower diameter: Average of 25 mm.
Flower, arrangement of petals: Free.
Flower, size of calyx: Calyx diameter average of 24 mm.
Color of calyx: 137B.
Flower stamen: Present.
Number of stamens per flower: Average of 26.
Number of sepals per flower: Average of 12.
Petal, length in relation to width: Equal, Average of 10 mm long and 9 mm wide.
Petal, color of upper side: NN155B.
Petal, color of lower side: NN155B.
Number of petals per flower: Average of 6.
Fruit, length in relation to width: Average of 51 mm long and 41 mm wide.
Fruit size: Average of 35 grams through the season for both primary and secondary fruit.
Fruit shape: Conical.
Fruit, difference in shape of terminal and other fruits: Slight.
Fruit color: 45A.
Fruit, evenness of color: Even or very slightly uneven.
Fruit glossiness: Strong.
Fruit, evenness of surface: Even or very slightly uneven.
Fruit, width of band without achenes: Absent or very narrow.
Fruit, positions of achenes: Below surface.
Achene color: 4A.
Fruit, position of calyx attachment: Inserted.
Fruit, attitude of sepals: Upwards.

Fruit, diameter of calyx in relation to fruit diameter: Slightly smaller.
Fruit, adherence of calyx: Weak.
Fruit firmness: Firm.
Fruit, color of flesh (excluding core): 33A.
Fruit, color of core: 41C.
Fruit cavity: Average of 4.4 mm.
Time of beginning of flowering: Early, starts in January to October.
Time of beginning of fruit ripening: Early, starts in February to November.
Type of bearing: Day neutral.

PLANT AND FOLIAGE COMPARISONS

Fruiting plants of 'UCD Valiant' are similar in height to 'Monterey', but slightly taller than 'Cabrillo' and 'San Andreas'. The spread is slightly more compact than 'Monterey' and 'Cabrillo' and more similar to 'San Andreas'. Leaves (including petioles) for 'UCD Valiant' are longer than for all three comparative cultivars. Color for the upper and lower levels of the leaves of 'UCD Valiant' are lighter green than 'Monterey' and 'Cabrillo' and more similar to 'San Andreas'. Serrations at midseason are more pointed than 'Monterey' and more similar in shape and number to 'Cabrillo' and 'San Andreas'. The stipule length of 'UCD' Valiant is shorter than all three comparative cultivars. Stolon production of 'UCD Valiant' is greater than 'San Andreas', but less than for 'Cabrillo' and 'Monterey'.

FLOWERING AND FRUITING COMPARISONS

'UCD Valiant' is similar to other California day-neutral cultivars (e.g. 'Cabrillo', 'Monterey' and 'San Andreas') in that it will flower independently of day length, given appropriate temperature and horticultural conditions. General tendency is for flowering to initiate earlier than the cultivars 'Monterey' and 'Cabrillo' and more similar to 'San Andreas'. The primary flowers for 'UCD Valiant' are similar in size to the comparative cultivars with a calyx that is slightly larger relative to the corolla on the primary fruit. The sepals for 'UCD Valiant' are similar in length and width compared to 'San Andreas', but shorter and narrower than 'Monterey' and 'Cabrillo'. The calyx of 'UCD Valiant' is variable (reflex to flat) more similar to 'Monterey' and 'San Andreas', and less reflexive than 'Cabrillo'. The fruit shape of 'UCD Valiant' can vary through the season, but is generally a conic fruit as compared to the long conic fruit of 'San Andreas', the short and rounded conic fruit of 'Cabrillo' and the short and slightly flattened conic fruit of 'Monterey'. External fruit color of 'UCD Valiant' is similar to 'Monterey', but slightly darker than 'Cabrillo'. The internal fruit color of 'UCD Valiant' is similar to 'Cabrillo', but lighter than 'Monterey'.

Achenes of 'UCD Valiant' are slightly indented in the fruit, comparatively similar to the fruit of 'Cabrillo' and 'San Andreas', whereas the achenes of 'Monterey' are more flat to the surface position.

What is claimed is:

1. A new and distinct cultivar of strawberry plant having the characteristics substantially as described and illustrated herein.

* * * * *